(12) United States Patent
Kornfeldt et al.

(10) Patent No.: US 6,874,356 B2
(45) Date of Patent: Apr. 5, 2005

(54) METHOD AND DEVICE FOR MONITORING AND CONTROLLING A PROCESS

(75) Inventors: Anna Kornfeldt, Västerås (SE); Thomas Liljenberg, Västerås (SE); Stefan Backa, Karlstad (SE); Claudio Pecorari, Västerås (SE); Eva Lundberg, Västerås (SE)

(73) Assignee: ABB AB, Västerås (SE)

( * ) Notice: Subject to any disclaimer, the term of this patent is extended or adjusted under 35 U.S.C. 154(b) by 0 days.

(21) Appl. No.: 10/703,493

(22) Filed: Nov. 10, 2003

(65) Prior Publication Data

US 2004/0106170 A1 Jun. 3, 2004

Related U.S. Application Data (63) Continuation of application No. 10/471,051, filed as application No. PCT/SE02/00430 on Mar. 8, 2002.

(30) Foreign Application Priority Data

Mar. 8, 2001 (SE) .............................................. 0100791
Mar. 8, 2001 (SE) .............................................. 0100792

(51) Int. Cl.[7] .......................... G01N 29/00; G01N 33/06
(52) U.S. Cl. ..................... 73/64.42; 73/32 A; 73/61.75; 73/64.53; 73/53.02
(58) Field of Search ............................. 73/64.42, 61.67, 73/61.71, 61.75, 61.79, 64.53, 865.5, 32 A, 53.02; 324/71.1, 457

(56) References Cited

U.S. PATENT DOCUMENTS

| | | | | |
|---|---|---|---|---|
| 3,774,717 A | * | 11/1973 | Chodorow ................. | 73/61.75 |
| 4,152,928 A | * | 5/1979 | Roberts ....................... | 600/447 |
| 4,384,476 A | * | 5/1983 | Black et al. ................ | 73/61.79 |
| 4,497,208 A | * | 2/1985 | Oja et al. ...................... | 73/584 |
| 4,825,688 A | * | 5/1989 | Kraus, Jr. et al. .......... | 73/61.75 |
| 4,848,139 A | * | 7/1989 | Blake-Coleman et al. . | 73/61.75 |
| 4,907,453 A | * | 3/1990 | Marlow et al. ............... | 73/584 |
| 4,959,228 A | * | 9/1990 | Skrgatic et al. ................ | 426/11 |
| 5,017,494 A | * | 5/1991 | Karube et al. ............ | 435/287.9 |
| 5,056,357 A | * | 10/1991 | Dymling et al. ........... | 73/54.41 |
| 5,060,507 A | * | 10/1991 | Urmson et al. ............ | 73/24.01 |
| 5,739,432 A | * | 4/1998 | Sinha .......................... | 73/579 |
| 5,837,885 A | * | 11/1998 | Goodbread et al. ......... | 73/32 A |
| 6,109,098 A | * | 8/2000 | Dukhin et al. ............. | 73/64.42 |
| 2003/0087802 A1 | * | 5/2003 | Urry ............................ | 514/2 |

FOREIGN PATENT DOCUMENTS

| | | | |
|---|---|---|---|
| DE | 4429809 A1 | * | 2/1996 |
| EP | 0302724 | | 2/1989 |
| JP | 6194345 A | * | 7/1994 |

OTHER PUBLICATIONS

English language abstract of DE04429809.*
Derwent abstract of DE 4429808.*
Hackley et al. J. Res. NIST, vol. 103, Apr. 1998, pp. 217–223.*
Henning et al. "In–line concentration measurement in comples liquids using ultrasonic sensors", Ultrasonics vol. 38, 2000 no month, pp. 799–803.*

(Continued)

Primary Examiner—Michael Cygan
(74) Attorney, Agent, or Firm—Venable LLP; Eric J. Franklin (57) ABSTRACT

A method and device for monitoring and controlling a pharmaceutical, chemical or food process, in which the biological activity and/or the bio-mass of micro-organisms in the process is monitored, and in which the state of the process is detected by monitoring viscosity and/or aggregate size and/or content of a dispersion of proteins, crystalline particles or fat droplets that are processed, respectively. The micro-organisms and/or bio-molecules produced in the process, and the proteins, crystals particles or fat droplets being processed are monitored by means of acoustic spectroscopy.

23 Claims, 6 Drawing Sheets

OTHER PUBLICATIONS http://www.dispersion.com/pages/newsletter/Newsletter3.pdf "Acoustics and Electroacoustics for Ceramics", Mar. 1999.*

Ishimori, Yoshio et al. "Determination of Microbial Populations with Piezoelectric Membranes", Applied and Environmental Microbiology, Oct. 1981, vol. 42, No. 4, pp. 632–637.* http://144.92.76.98/GUNA/evaluatingmilk94.PDF "Evaluating Milk Coagulation with Ultrasonics", Oct. 1994.*

Marshall, Thomas et al. "Monitoring the crystallization from solution of a reactive dye by ultrasound", Meas Sci Technol. vol. 11, 2000 no month, pp. 509–517.*

Edwin L. Carstensen and Herman P. Schwan; Absorption of Sound Arising from the Presence of Inact Cells in Blood; The Journal of the Acoustical Society of America; Feb., 1959;pp. 185–189; vol. 31, No. 2.

* cited by examiner

METHOD AND DEVICE FOR MONITORING AND CONTROLLING A PROCESS

This application is a continuation of U.S. Ser. No. 10/471,051 filed Jan. 28, 2004 which is a 371 PCT/SE02/00430 filed Mar. 8, 2002.

TECHNICAL FIELD

The present invention relates to a method and device for monitoring and controlling critical parameters, such as particles, bio-molecules and viscosity, in industrial pharmaceutical, food and chemical processes.

In particular, the present invention relates to a method and a device for monitoring and controlling a fermentation process by monitoring the biological activity, the bio-mass of micro-organisms and/or produced bio-molecules in the process.

The present invention also relates to a method and a device for monitoring and controlling viscosity and/or aggregate size and/or content of dispersions of proteins, crystalline particles or fat droplets during processing thereof. These parameters are altered or adjusted in order to obtain a desired product quality, particularly related to a food product, such as a dairy product. The process may be a denaturation, homogenisation, crystallisation or a fermentation process.

Monitoring should be understood in a broad sense, and will include the execution of measurements the result of which depends on the condition and content of the proteins, crystalline particles or emulsion droplets.

Denaturation should be understood as any kind of altering of the natural state of the proteins, and also alterations of the size or size distribution of agglomerates thereof.

Homogenisation should be understood as any kind of altering of the particle size distribution of a dispersion or an emulsion.

Crystallisation should be understood as any kind of nucleation and/or formation of solid particles.

BACKGROUND OF THE INVENTION

Fermentation processes are widely used for the purpose of producing pharmaceutical bio-molecules to be used as the active agent in pharmaceutical preparations as well as for a number of other types of bio-molecules e.g. enzymes, organic acids etc.

Fermentation processes for production of pharmaceutical bio-molecules by micro-organisms are very difficult to control. Due to this some processes may have a recovery of the bio-molecules produced of only 50% or even much lower. The problem is that it is very difficult to get a sensor system that can handle a dynamic complex fluid, which also is bubbling and foaming, and monitor the activity or bio-mass of the micro-organisms, e.g. growth of the bio-mass. A sensor system enabling both the characterisation of a complex fluid, in which gas bubbles and foam are produced, and the monitoring of the bio-mass growth is not yet available on the market.

On-line measurement of the biological activity/bio-mass of the micro-organisms in the process is desired in order to make it possible to instantly adjust the process based on such measurement.

It should be noted that, normally, the micro-organisms and the bio-molecules produced by the process are present as a dispersion in a fluid, normally a liquid.

The rheological properties of food products, such as dairy products, are very important as they determine quality aspects such as product stability, taste and mouth feel. These properties are defined by bio-molecules and/or emulsion droplets and/or crystalline particles and their content and quality. Different processes, for example denaturation of whey, homogenisation of milk, and crystallisation of detergents are used to obtain the desired properties.

Whey is a milk product obtained as a by-product during, for example, cheese production. The whey obtained during such production is dried, preferably spray dried, or concentrated by membrane technologies, and used in other food products. The surplus is sometimes used as fodder.

The original protein molecule or bio-molecule in diluted whey has a three dimensional structure with inter-chain bonding. The protein molecules are to some degree changed during the denaturation process due to pH and temperature changes. Thereby, the protein is denatured to a varying degree. Accordingly, the protein takes part in a denaturation process.

The denaturation alters the functional character of the whey. For example, the interaction with water and thus the solubility and viscosity when re-dispersed is altered by the denaturation. Thus, both the rheological properties and the aggregate size distribution is altered. In order to obtain a high quality whey product and, simultaneously, to reduce total costs for the production thereof, it is important to control the degree of denaturation continually or continuously during the process.

During homogenisation of an emulsion, for example milk, the fat droplets are subjected to shear forces and disrupted to various degrees. A smaller droplet size distribution is obtained and thus the stability of the emulsion is increased. Also the taste and mouth feel of the product is altered. It is important to control the droplet size distribution and viscosity to obtain desired product quality.

Crystallisation processes are applied in manufacturing of many different types of chemicals such as pharmaceuticals, detergents, enzymes, fertilisers, insecticides, herbicides as well as inorganic salts. Of special interest is also crystallisation based separation systems. The most crucial parameters to monitor for control of these processes are particle-size distribution and rheological properties. If these can be controlled by a reliable monitoring system higher product quality, e.g. purity and narrower particle size distribution, as well as better down stream processing conditions, e.g. filtration, can be obtained.

Prior Art

Known processes and devices for monitoring and controlling a fermentation process use measurement of the glucose content and supply and measurement of the oxygen content in the liquid as well as alkali used to adjust the pH. Recent techniques use bio-sensors to monitor the composition of the liquid as well as the composition of the air from the fermentor. Thereby, an indirect measurement of the biological activity is obtained.

However, a drawback of such known processes is that they are a measure of the nutrient composition and oxygen content and do not monitor the actual biological process or production of bio-molecules. The oxygen content in the liquid is not always a good indication of the bio-mass activity or how much oxygen the micro-organisms really are able to assimilate, since the oxygen intake of the latter during the process is unknown. Therefore, such measurements of oxygen content might lead to an incorrect information about the biological activity, e.g. the content and viability of the micro-organisms in the fermentation process.

Laboratory methods for off-line analysis are used but they are too slow to be used for controlling the process.

There is thus a need for direct methods to monitor micro-organism production as well as the quality of the produced bio-molecules.

Further, according to prior art, one way of obtaining information about dispersions, e.g. the degree of denaturation, emulsion droplets or solid crystals in a process is to measure the particle size distribution of the agglomerates, particles or emulsion droplets by means of laser technique or ultra sound. These measurement are off-line measurements. Such measurements have the disadvantage of being much slower, the result thereof being obtained too late to enable a swift and timely adjustment of process control parameters such as temperature and pH (for the denaturation process) and temperature and pressure (for the homogenisation and crystallisation processes) based on those measurements.

THE OBJECTS OF THE INVENTION

A first main objective of the present invention is to present a method and a device by means of which an on-line measurement of the biological activity, in particular the micro-organism content and viability and/or the concentration and quality of the bio-molecules produced in a fermentation process, can be obtained.

A further objective is to present a method and a device that avoids noticeable degeneration of micro-organisms that are subjected to the on-line measurement of their biologic activity.

A further objective of the invention is to present a method and a device that makes an efficient, uncomplicated and reliable measurement of the biological activity/bio-mass of the micro-organisms possible.

A second main objective of the invention is to present a method and a device that makes it possible to measure on-line the degree of denaturation in a denaturation process, the degree of homogenisation in a homogenisation process, and the degree of crystallisation in a crystallisation process, thereby making it possible to immediately make the necessary adjustments on process parameters based on the measured viscosity, agglomerate or particle size distribution.

The invention shall also be non-complicated, economically advantageous and suitable to implement on industrial processes such as denaturation, homogenisation, crystallisation, fermentation, and acidifying of dairy products.

BRIEF DESCRIPTION OF THE INVENTION

The first man objective of the invention is achieved by means of the initially defined method, characterised in that the micro-organisms and/or bio-molecules produced in the process are monitored by means of acoustic spectroscopy.

Acoustic spectroscopy is a technique that investigates the dependence of the acoustic properties of a fluid on frequency. The frequency of the propagating acoustic waves ranges between 0 and 20 kHz. The use of acoustic waves is advantageous since such waves have a penetration range in the micro-organism culture large enough to guarantee a reliable result. The results of the acoustic spectroscopy depend on physical properties, such as compressibility, density and rheology. These are governed by the bio-mass (or total bio-mass) or the biological activity of the micro-particles since dead and alive micro-particles and the produced bio-molecules affect the propagation of the acoustic waves differently. Hence, it is the biological activity/bio-mass of the micro-organisms that is monitored and that is predicted by means of the inventive method. Preferably, the values of essential process control parameters such as the amount of nutrient solution added to the micro-organisms during the fermentation and/or the aeration of the liquid/micro-organism dispersion is based on the result of the measurement achieved by means of the acoustic spectroscopy. Further, the monitoring parameter values can be used to change certain process stages, e.g. if a value reaches a certain limit a process at a certain stage has to slow down or to be temporarily altered in order to achieve an optimal quality of the produced product.

The monitoring of the biological activity of the micro-organisms by means of acoustic spectroscopy requires the measurement of changes of acoustic wave properties caused by the micro-organisms.

Normally the micro-organisms define micro-particles dispersed in a fluid, preferably a liquid.

The micro-organisms comprise any living agent, preferably anyone in the group comprising bacteria, fungi, animal cells, vegetable cells, insect cells, or mammalian cells and are able to or manipulated such that they produce a predetermined type of bio-molecule. The bio-molecules produced by means of the micro-organisms are used as an active agent in a pharmaceutical preparation.

Monitoring the biological activity, as used in this context, comprises monitoring the content and/or viability of micro-organisms as well as quality and/or content of bio-molecules produced by the micro-organisms in the liquid. It should be noted that the micro-organisms and bio-molecules are dispersed in a liquid, such as water.

The micro-organisms are dispersed in a liquid which is conveyed through a tube, and the acoustic waves applied to micro-organism/liquid dispersion propagate in the direction of the tube axis. In particular for lower frequencies, in the plane wave frequency region, the acoustic waves will be transmitted in a direction along the tube axis. A fermentation process normally takes place in a vessel. The use of a tube with inlet from the bottom of the fermentation vessel makes it possible to significantly reduce the amount of air bubbles and foam that will be present in the culture liquid taken from said vessel. Such bubbles and foam would have a detrimental effect to the reliability of the acoustic spectroscopy if not significantly reduced. Preferably the inlet into the tube from the fermentation vessel, or the corresponding outlet from the vessel, is designed so as to reduce or avoid bubbles and foam in the sample of culture conducted through the tube. Another way of degassing the liquid is to include a degassing step in the tube or tube line.

At a first end thereof the tube is connected to a fermentation vessel in which the fermentation process takes place, and the dispersion of the micro-organisms and the produced bio-molecules is delivered to the tube via an outlet from the fermentation vessel.

At its other end, the tube is connected to an inlet to the fermentation vessel, thereby defining a closed loop via which the micro-organisms that are subjected to the acoustic spectroscopy are circulated from and to the fermentation vessel.

The fluid containing the micro-organisms subjected to acoustic spectroscopy is preferably simultaneously subjected to ultrasonic waves for the purpose of sensing different responses of the micro-organisms to a perturbation on the micro-organisms caused by the acoustic waves.

The ultrasonic waves are transmitted such that they propagate in a direction cross-wise, preferably perpendicularly, to the direction of the acoustic waves, the latter propagating in a direction generally parallel to the axis of the tube.

The first main objective of the invention is also achieved by means of the initially defined device for monitoring biological activity of micro-organisms in a fermentation process, characterised in that it comprises a means for subjecting the micro-organisms and/or bio-molecules produced in the process to acoustic spectroscopy.

The device preferably comprises a tube for transport of the dispersion, and a transmitter for directing acoustic waves through the dispersion in the length direction of the tube. The liquid dispersion is composed of micro-organisms and bio-molecules produced thereby. The acoustic waves propagate through the dispersion.

According to a preferred embodiment, the device comprises a plurality of acoustic sensors arranged as an array around or along the tube for the purpose of measuring the acoustic waves generated in the liquid containing the micro-organisms by the transmitter.

According to another preferred embodiment, the device comprises a hydrophone as a transducer and/or projector arranged at the inlet of the tube, and electrically driven by a voltage to generate a random white sound in the liquid.

According to a further development of the device, the latter comprises an ultrasonic transducer for directing ultrasonic waves over a cross section of the tube where the micro-particles are subjected to the acoustic waves.

According to another development, the device comprises a plurality of sections of pipes made of polymer material inserted along the tube, and around these sections-piezoelectric wires are arranged to work as acoustic sensors.

Changes of properties of the micro-organisms and their cell walls, e.g. viability and assimilation of products, have an impact on the compressibility and thus these type of properties can be monitored.

Preferably, the device also comprises a pump to facilitate the flow of a sample of micro-organisms from a fermentation vessel in which the fermentation process takes place to the tube in which the acoustic spectroscopy is executed, the tube being connected at one end thereof to the fermentation vessel via an outlet from the fermentation vessel.

At its other end, the tube shall be connected to an inlet to the fermentation vessel such that the micro-organisms taken from the fermentation vessel and transported through the tube can be returned to the fermentation vessel for further use in the fermentation process.

The invention also relates to the use of acoustic spectroscopy for the purpose of monitoring the biological activity/bio-mass of micro-organisms and/or the bio-molecules produced thereof in a fermentation process. Preferably the micro-organisms comprise dead and alive micro-organisms, and the content and viability is measured by means of the acoustic spectroscopy. According to a preferred embodiment, the micro-organisms comprise any living agent, preferably one from the group comprising bacteria, fungi, animal cells, insect cells and mammalian cells.

The second main objective of the invention is achieved by means of the method defined initially, characterised in that at least a part of the proteins, crystalline particles and/or emulsion droplets are monitored by means of acoustic spectroscopy. The principle of the invention is to take advantage of the relatively long penetration range of acoustic waves into pipes and other process vessels containing process materia, such as bio-molecules in the form of soluble non-fat components, e.g. proteins and carbohydrates, or emulsion droplets, e.g. fat droplets or crystalline particles in food products, such as dairy products. The long penetration range promotes on-line measurement of propagating acoustic waves in process pipes or vessels. The term on-line measurement should be understood in a broad sense also comprising in-line and at-line measurement. Since the effect of such components on the acoustic wave propagation changes with changing degree of aggregate size distribution and fluid viscosity, the result of such acoustic spectroscopy makes it possible to determine e.g. the degree of denaturation or homogenisation as this has impact on the compressibility. It should be noted that acoustic waves have a frequency in the range of 0–20 kHz, and that the bio-molecules at least initially are present as micro-particles having a size within the micrometer range, up to 1000 micrometer.

A denaturation process is controlled by means of heat and/or pH adjustment, such adjustments being based on the acoustic spectroscopy. Homogenisation and crystallisation processes are controlled by means of temperature, agitation and pressure adjustments based on the acoustic spectroscopy.

The bio-molecules/fluid subjected to the acoustic spectroscopy are flowing through a tube, normally a tube included in a process line in which the denaturation is a vital step. Thereby, the bio-molecules are dispersed in a fluid, preferably a liquid, as they flow through the production line and are subjected to said denaturation.

According to one embodiment the acoustic waves, that the proteins and fat droplets are subjected to, are transmitted along the tube axis; in one embodiment in a direction generally parallel to the flow direction of the bio-molecules/fluid.

The dispersion of proteins or fat droplets in a liquid may also be subjected to an ultrasonic measurement, preferably across the tube channel, and the process is controlled based on the acoustic spectroscopy with regard taken to the result of the ultrasonic measurement.

The molecules are dispersed in a liquid, but are subjected to heat treatment or pH adjustment during the denaturation process, and to pressure change during homogenisation processes.

The dispersion comprises proteins subjected to denaturation in a process for preparing a food product, preferably a dairy product, and most preferably whey.

The dispersion may also comprise fat droplets subjected to homogenisation of a dairy product, such as milk.

The dispersion may also comprise nuclei, subjected to crystallisation, such as pharmaceutical particles.

The measurement by means of acoustic spectroscopy is an on-line measurement executed in a process line in which said denaturation or homogenisation process takes place.

The second main objective of the invention is also achieved by means of a device as initially defined, characterised in that it comprises a means for subjecting the proteins, crystalline particles and/or fat droplets dispersed in liquid to acoustic spectroscopy. Such means preferably comprises an acoustic wave transmitter and one or more acoustic sensors. The sensors may comprise hydrophones, strain, displacement, velocity or acceleration sensors.

According to one embodiment of the invention the device comprises a tube through which the dispersion flows while being subjected to the acoustic spectroscopy. The acoustic transmitter should be arranged such that the acoustic energy is transmitted to the fluid in the tube. The acoustic sensors may be arranged at one or more locations along and/or around the tube. Both transmitter and sensors may be arranged with or without direct contact (preferable in food applications) with the fluid in the tube.

According to another embodiment, the device comprises a hydrophone as a transducer and/or projector arranged at the inlet of the tube, and electrically driven by a voltage to generate a random white sound in the liquid.

According to another development, the device comprises a plurality of sections of pipes made of polymer material inserted along the tube, and around these sections-piezoelectric wires are arranged to work as acoustic sensors.

Preferably, the tube is a tube in a process line for the production of a food product, preferably a dairy product, and most preferably a process in which whey is denatured or fat droplets are homogenised, The tube may also be a tube in a process line for the production of solid particles by crystallisation.

The device should comprise an ultrasonic transducer for transmitting ultrasonic waves through the dispersion that are subjected to the acoustic spectroscopy. The use of ultrasonic transducers alone for the purpose of process monitoring is already known as an off-line measuring method. Here, however, the ultrasonic transducer is used as a supplement to the acoustic spectroscopy equipment in order to determine reference or set values of the acoustic spectroscopy measurement. The ultrasonic transducer is preferably arranged as a device not in direct contact with the fluid in the tube and directs ultrasonic waves in a direction cross-wise to the tube channel.

The invention also relates to the use of acoustic spectroscopy for monitoring a process in which the state of the process is detected by monitoring viscosity and/or aggregate size and/or content of dispersions of proteins, crystalline particles or fat droplets that are processed.

In particular, it relates to the use in which the denaturation process is a process for the production of a food product, preferably a dairy product, most preferably a process in which whey is denatured or a process in which fat droplets are homogenised.

Further features and advantages of the present invention will be presented in the following detailed description and in the accompanying drawings.

BRIEF DESCRIPTION OF THE DRAWINGS

Embodiments of the invention will now be described by way of example with reference to the accompanying drawings, in which.

DETAILED DESCRIPTION OF THE INVENTION

Figure 1:
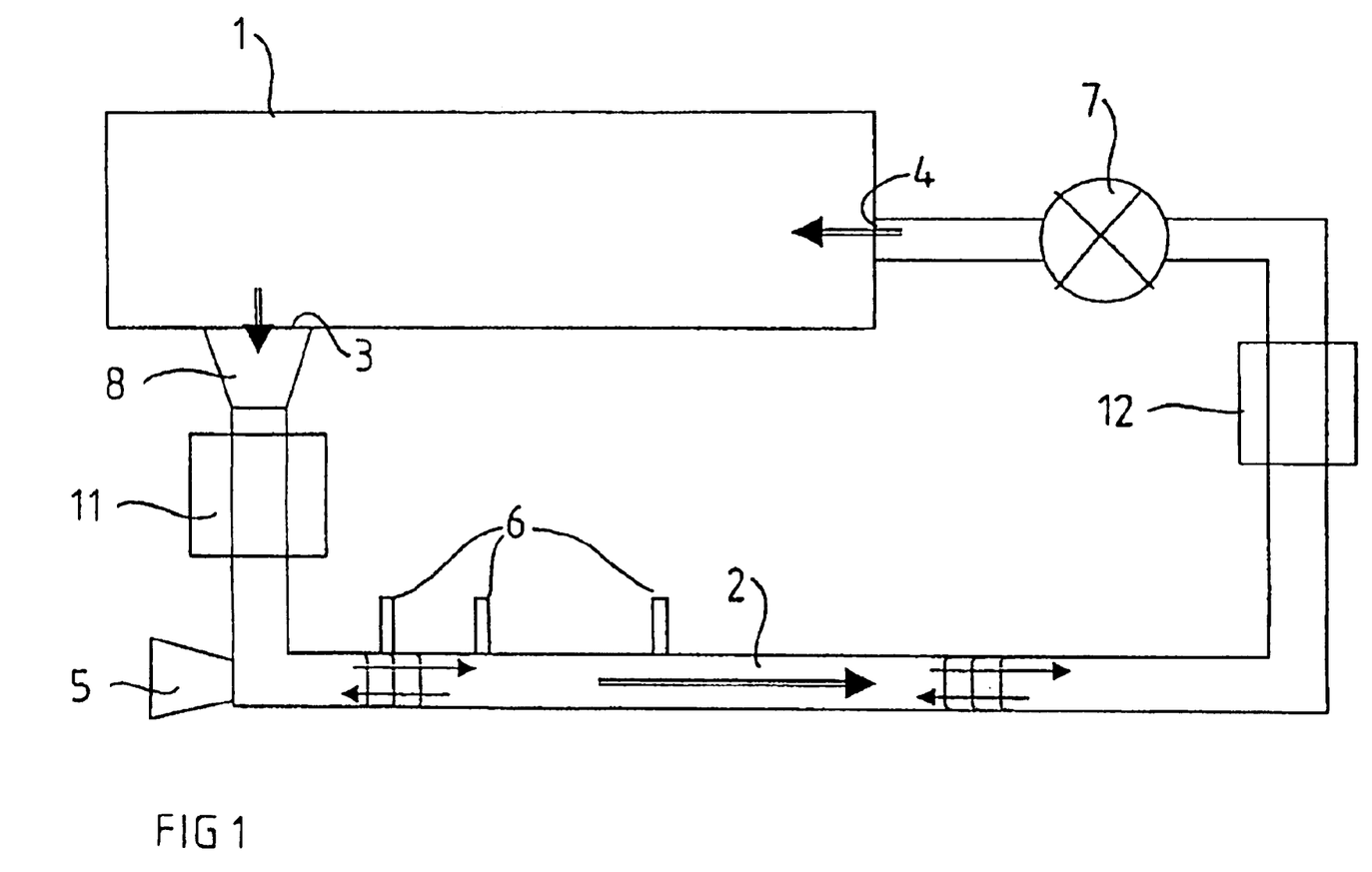
FIG. 1 is a schematic view of a first embodiment of a device according to the invention.

FIG. 1 shows a device for controlling and monitoring a fermentation process. The process comprises mixing of a base culture of micro-organisms such as bacteria, fungi, animal, vegetable, insect, or mammalian cells with a nutrient solution, tempering of the mixture, aeration (addition of oxygen), stirring, mixing, creation and extraction of a culture fluid. The culture fluid is then used for the purpose of producing a pharmaceutical or other chemical product. The micro-organisms are dispersed as micro-particles in the fluid, which is preferably a liquid.

The device comprises a fermentation vessel 1 for batch type fermentation, a so-called fermenter. It also comprises a tube 2 connected at a first end thereof to an outlet 3 from the fermentation vessel 1, and connected at its other end to an inlet 4 to the fermentation vessel 1.

There is also arranged an acoustic wave-source or wave transmitter 5 and a plurality of acoustic sensors 6, such as pressure, displacement, velocity, acceleration or strain sensors, along the tube 2. Sterilisable hydrophones, working as sensor and transmitter (transducer) respectively, positioned in direct contact with the liquid can also preferably be used as an acoustic source. The wave-source 5 and sensors 6 are used for the purpose of subjecting a sample of the culture liquid taken out from the fermentation vessel 1 to acoustic spectroscopy in order to measure the content and viability of micro-organisms in the culture. The measurement of the activity of the micro-organisms by means of acoustic spectroscopy is an on-line measurement. The values of fermentation control parameters such as amount of added nutrient solution, aeration, and pH in the fermentation vessel 1 etc. are determined and controlled based on the monitoring or on-line measurement of the micro-organism activity or the bio-mass. The monitoring can also be used to determine an optimum process level. Preferably, multivariate data analysis is used for predicting the biological activity/bio-mass or produced bio-molecules based on the on-line monitoring and for determining the values of the control parameters.

Moreover, the device comprises a pump 7 for pumping the sample of micro-organisms through the tube and back to the fermentation vessel 1. The inventive device also comprises means 8 for reducing the presence of bubbles and foam in the culture sample transported into and through the tube 2. The anti-bubble means could be any mechanical device, such as a cyclone, suitable for the given purpose, and is preferably arranged at the inlet or at least up-stream the portion of the tube 2 in which the sample is subjected to the acoustic spectroscopy measurement.

The tube 2 is preferably made of a rigid material such as stainless steel.

In an alternative arrangement the tube should be made of a less rigid material, preferably a polymer, in sections where the acoustic sensors 6 are arranged. Such a soft and dampening material may also preferably be used in the tube section between the outlet 3 and the location of the acoustic wave transmitter 5, as well as in the section passing the pump 7.

It should be understood that the device also comprises equipment that is normally needed in the fermentation process but not shown here. Such equipment may include inlets, tubes and spargers for air, stirrers and impellers, extraction outlet for the culture fluid (drain point), inlets for base culture and nutrient solution, etc. The invention is thus not delimited to any specific type of fermenter but applicable to fermenters and fermentation processes in a broad sense. The inventive device and method is thus applicable to batch as well as continuous processes. Preferably, the device comprises one or more units for controlling the process parameters based on the monitored biological activity. Such units may comprise a processor for signal processing and multivariate data analysis and be operatively connected to the source 5 and/or the sensors 6. Preferably, the conditions, i.e. biological activity, in the process are predicted and suitable control parameter values are determined by means of such a unit or units based on the monitored biological activity.

During the fermentation process, a small amount of culture liquid is taken out via the outlet 3 and pumped by means of the pump 7 through the tube 2 and back to the fermentation vessel via the inlet 4. Samples need not be taken out batch-wise but there may as well be provided for a continuous flow of culture liquid through the tube 2.

The culture liquid should be affected as little as possible during the measurement in the tube 2, that is the content and viability of the micro-organisms must not be noticeably reduced, and the conditions must not be changed to the extent that the measurement result does not correspond to the condition prevailing in the fermentation vessel 1. Therefore, the residence time of the sample of culture liquid containing the micro-organisms in the tube 2 is optimised, depending on type of culture of course, but normally must not exceed approximately 30 seconds.

The acoustic source 5 is arranged at one end of a straight portion of the tube. Acoustic waves propagate mostly in the length direction of said portion. The source is arranged outside the tube 2, in contact with the liquid via a membrane, i.e. not in direct contact with the culture liquid, and does not constitute a physical hinder for the culture liquid. The acoustic source can however also be a hydrophone, as mentioned above, that is electrically driven by a voltage to generate a random white sound in the liquid. The hydrophone can be in direct contact with the liquid.

Figure 2:
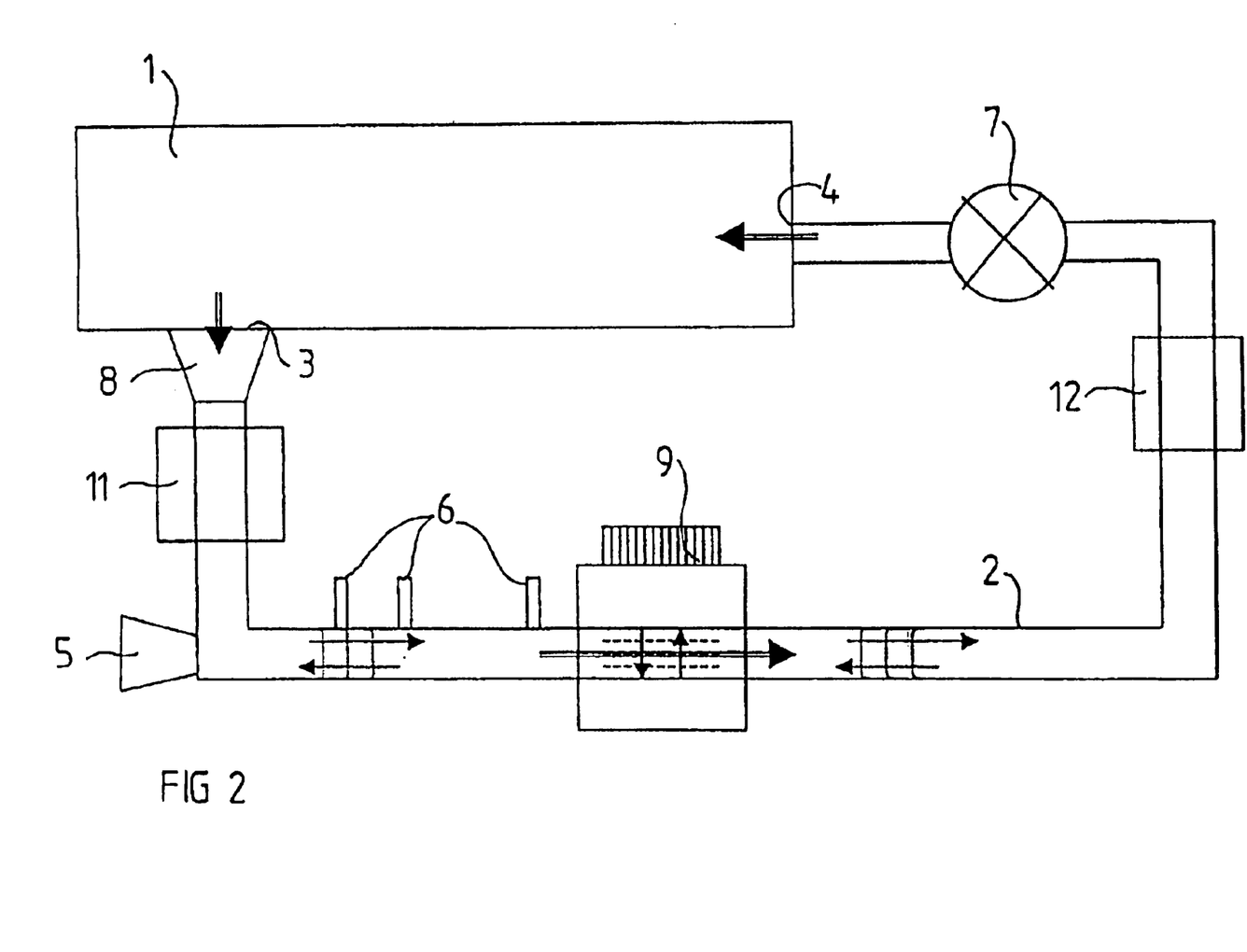
FIG. 2 is a schematic view of a second embodiment of the device according to the invention.

FIG. 2 shows a further development of the embodiment shown in FIG. 1. Here, the device also comprises an ultra-sound transducer 9. The transducer 9 is arranged as a clamp-on device on the tube 2 and has a well defined geometry, preferably rectangular cross section with plane surfaces perpendicular to the transmitted ultrasonic waves transmitted into the fluid. Accordingly, it is not in direct contact with the culture liquid and does not constitute a physical hinder for the culture liquid. The ultra-sound transducer 9 is used for transmitting ultrasonic waves into the culture liquid and detecting to what extent the ultrasonic waves are affected by the culture liquid. The transducer 9 transmits ultra-sound cross-wise, preferably perpendicularly to the flow direction of the culture liquid as well as to the propagation direction of the acoustic waves. It should be understood that the culture liquid defines the medium via which the acoustic and ultrasonic waves propagate.

Figures 4, 5:
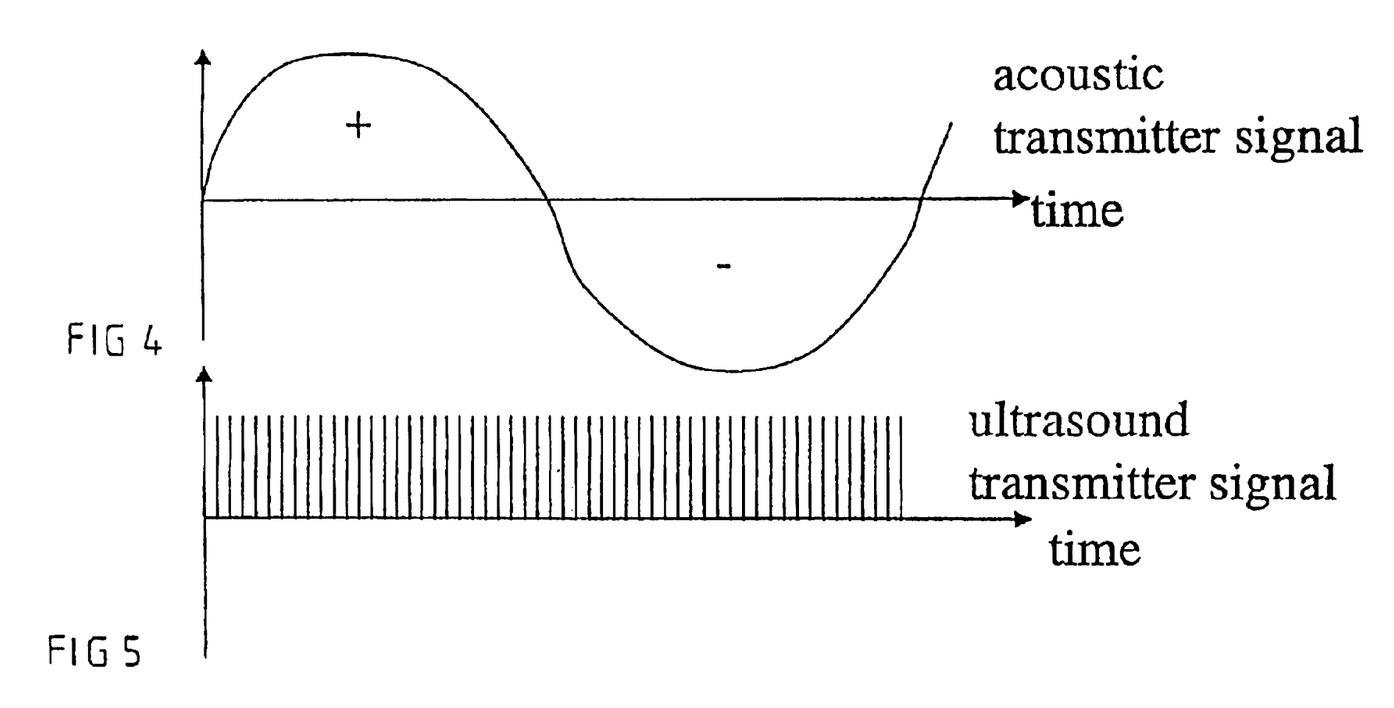
FIG. 4 is a diagram showing the dynamic pressure wave of alternating positive and negative pressures around a mean value generated by an acoustic source or transmitter.
FIG. 5 is a diagram showing the relation between ultrasound transducer waves and time.

The acoustic waves will cause a perturbation in the micro-organism/liquid dispersion. As seen in FIG. 4 the acoustic source or transmitter 5 will generate a dynamic pressure wave of alternating positive and negative around a (large) mean value. The acoustic waves will have much lower frequencies (0–20 kHz) than the ultrasonic waves (>100 kHz) (FIG. 5). This allows many ultrasound measurements being made during one period of the acoustic signal.

For the example of a sine wave, the acoustic pressure will be positive during half of the period and negative during half of the period (FIG. 4). This allows ultrasound measurements to be made both for positive and negative acoustic pressure (FIG. 5). If the measured ultrasound response of the fluid during positive acoustic pressure is different from the measured ultrasound response of the fluid when the acoustic pressure is negative, the difference between those two signals will give additional information about the fluid properties. The resulting data is by nature two-dimensional, which allows three-way multivariate data analysis, increasing the robustness of the method.

To further increase the sensitivity of the method several sensors 6 arranged in an array can be used. The array arrangement can both be in the axial direction of the tube 6 and around the circumference. The distance between the sensors 6 in axial direction will determine the useful frequency range. A large distance permits measurements for lower frequencies and a small distance permits measurements for higher frequencies. Arranging the sensors 6 to have both at least one shorter distance and at least one longer distance for sensor separation will increase the useful frequency range and the robustness of the method.

In a fluid-filled tube 2 there may be strong interaction between the pressure pulsations in the fluid and the vibrations of the tube walls and the surrounding structure. Sensors 6 may be arranged to obtain as a complete picture as possible of the behaviour in both fluid and structure to further increase the robustness of the method.

Figure 3:
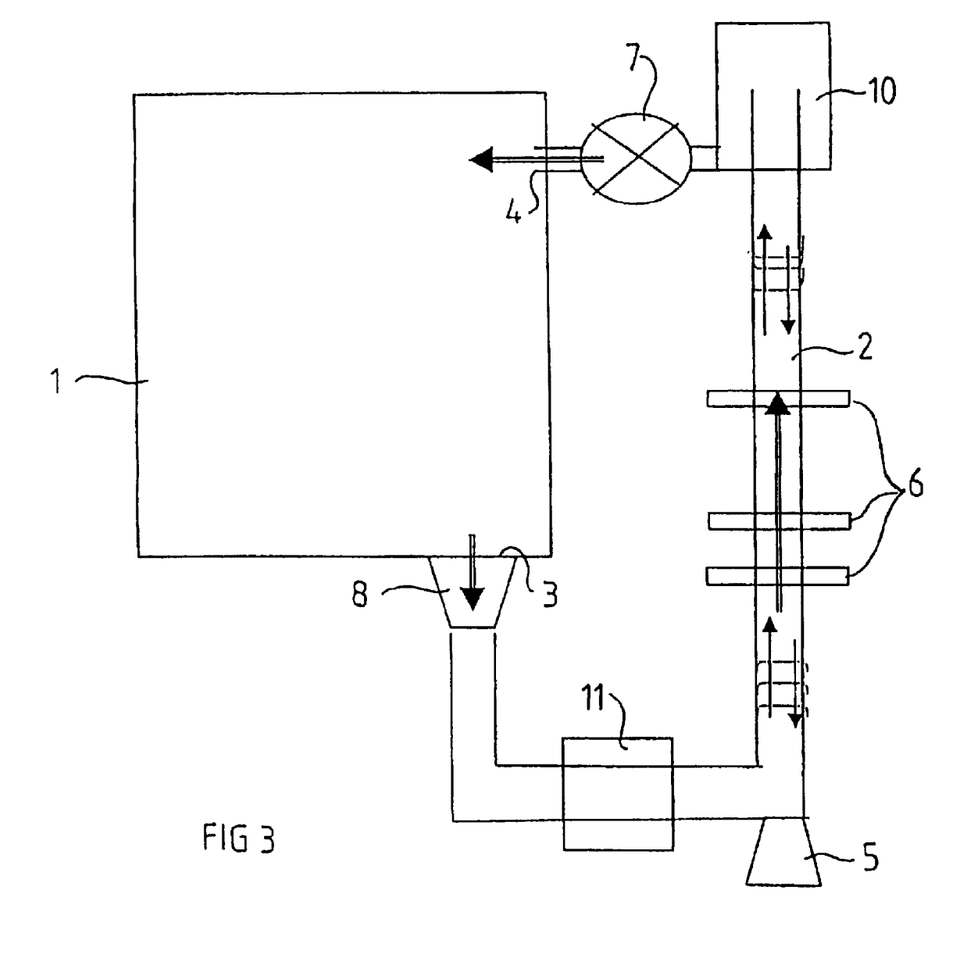
FIG. 3 is a schematic view of a third embodiment of the device according to the invention.

In FIG. 3 a further embodiment of the inventive device is shown, which comprises an alternative arrangement of the tube 2 in order to reduce disturbances caused by the pump 7. Here, the portion of tube 2 along which the acoustic waves are transmitted is inclined from a purely horizontal direction, and is more precisely vertical. The part of the tube 2 upstream the pump 7 protrudes into a chamber 10. The pump 7 is arranged downstream the chamber 10. The liquid level in the chamber 10 is such that there is always a sharply defined upper level of liquid in the tube part projecting into the chamber 10. Preferably, the level of the liquid in the chamber is always below the level of the outlet of the part of the tube 2 upstream the chamber.

The inventive device shown comprises one or more acoustic sound silencers, in FIGS. 1 and 2 an upstream and a downstream acoustic sound silencer 11, 12 (upstream and downstream with regard to the acoustic transmitter). The embodiment shown in FIG. 3 only presents an upstream silencer 11. Such silencers reduce the pressure pulsations and/or tube vibrations from different parts of the system, thereby improving the measurement conditions.

The application of the inventive method and device for controlling and monitoring fermentation process has been described by way of example. It is evident that a man skilled in the art would be able to derive from the above information a plurality of alternative embodiments all of which are still within the scope of invention as defined in the enclosed patent claims supported by the description and the accompanying drawing.

For example, it should be realised that the invention is applicable to arrangements for continuous fermentation as well as the batch wise process described above by way of example.

The application of the inventive method and device for controlling and monitoring a denaturation, homogenisation or a crystallisation process will be described in the following.

Figure 6:
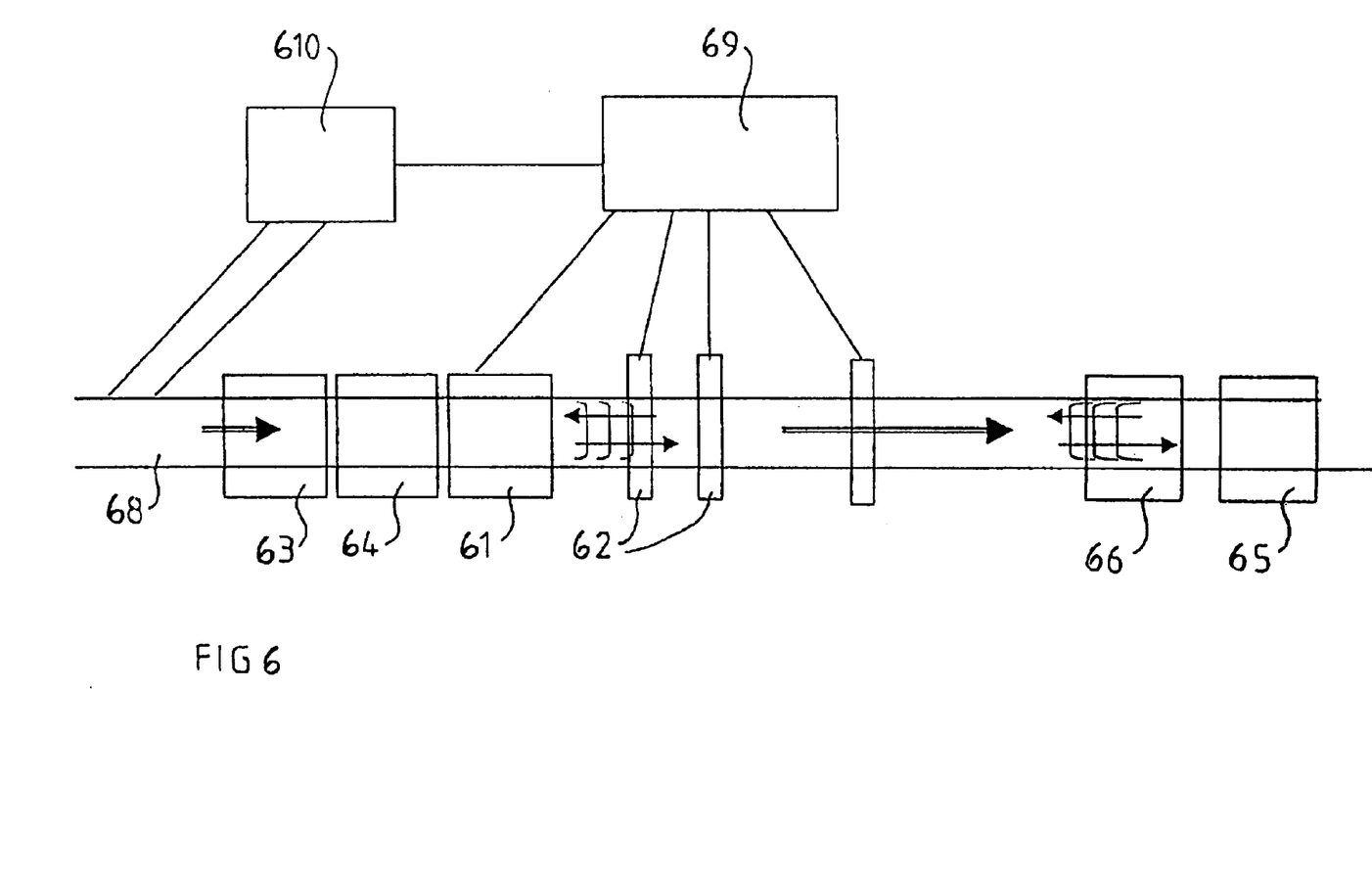
FIG. 6 is a schematic view of a preferred embodiment of the inventive device.
Figure 7:
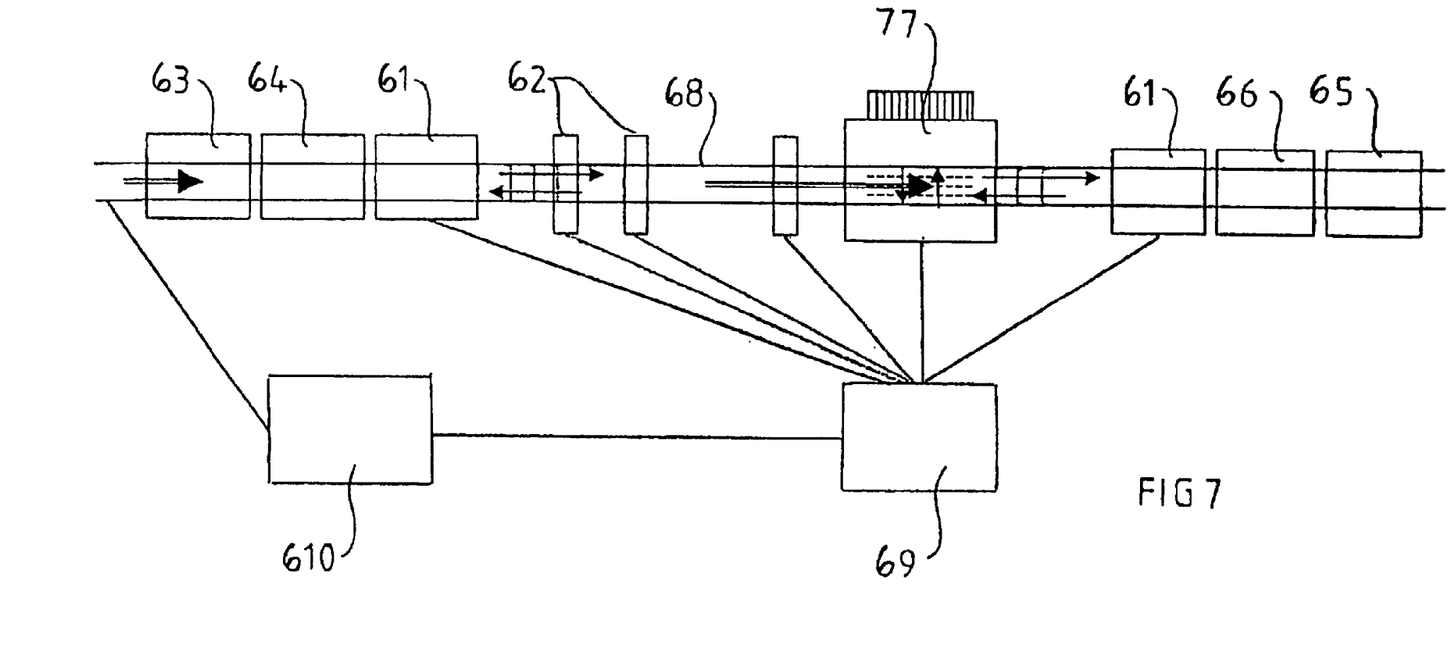
FIG. 7 is a schematic view of an alternative embodiment of the inventive device.

Generally, as shown in FIGS. 6 and 7 the inventive device or system consists of one or more acoustic transmitters 61 and one or more acoustic sensors 62. The system may also consist of one, a few or all or the following components: an upstream silencer 63, an upstream acoustic impedance 64, a downstream silencer 65 and a downstream acoustic impedance 66 and an ultrasound transducer 77 (as shown in FIG. 7).

In an industrial application the measurement can often be disturbed by other machinery such as pumps or motors, or by components such as valves or other discontinuities in the tubing. In certain applications, there may be a need of improving the measurement conditions by introducing a silencer 63, 65 upstream and/or downstream. The silencer 63, 65 will reduce the pressure pulsations and/or the tube vibrations from other parts of the system, to limit the disturbances.

By introducing an acoustic impedances 64, 66, the acoustic system will be better defined, allowing better analysis and signal processing of the collected data.

An ultrasound transducer 77, which can transmit and receive ultrasound signals can also be included in the inventive system.

In FIG. 6, there is shown a process line tube 68 in which a dispersion of proteins, crystalline particles or fat droplets in liquid, preferably water, is conducted. In a preferred embodiment, the dispersion comprises a food product, such as dairy product.

The process in which the tube 68 is used is for example a denaturation process. Here, the denaturation comprises the denaturation of protein molecules in a dairy product, more precisely whey. Alternatively the process is a homogenization process in which the dispersion comprises fat droplets subjected to homogenisation or a crystallisation process in which the dispersion comprises crystalline particles.

The device in FIG. 6 comprises means for acoustic spectroscopy in the form of an acoustic transmitter 61 and one or more acoustic sensors 62 arranged along the tube 68. The acoustic transmitter 61 transmits acoustic waves (f=0–20 kHz, preferably 100–5000 Hz, more preferred 100–3300 Hz) through the dispersion in the tube, and the sensors 62 sense the waves. Differences in the degree of e.g. denaturation will result in a change in the way the acoustic waves are affected by the dispersion, or the whey. Thereby, the degree of denaturation can be detected and measured by the inventive device.

The viscosity in a fluid will affect the attenuation of the propagating wave. The attenuation of the acoustic wave will include both a dissipation of the fluid and an attenuation due to fluid-wall interaction in the wall boundary layer. The measured attenuation will depend on, for example, frequency, temperature, the tube dimensions and tube properties, fluid bulk properties such as sound velocity, density and dissipation and size, properties and concentration of the dispersions. Most of the above-mentioned factors can be controlled and some can be neglected under certain conditions. Other factors can be included in a calibration procedure. The preferred tube for measurement is wide enough in relation to the fluid properties to allow actual wave propagation rather than diffusion of the acoustic wave.

As shown in FIG. 6 the data obtained by the means 61, 62 for acoustic spectroscopy are preferably subjected to signal processing and multivariate data analysis in order to monitor the degree of denaturation, homogenisation or crystallisation. A unit 69, such as a computer or any processor, provided with software adapted to perform said signal processing or multivariate analysis, is therefore operatively connected to the means 61, 62 for acoustic spectroscopy. It should be understood that the unit 69 is only shown by way of example. It need not be a separate part but could of course be an integrated part in one or more of the sensors 62.

Based on the multivariate analysis performed by means of the unit 69 process parameters affecting the denaturation process are controlled or adjusted. Typically, such parameters comprise heating or cooling the dispersion (temperature-affecting parameters) and/or adjustment of pH-value or of pressure of the dispersion. Only schematically there is shown a unit 610 for controlling or adjusting such process parameters. The control and adjustment unit 610 is operatively connected to the multivariate analysis unit 69. In absence of such a multivariate unit 64, the control and adjustment unit 610 may be directly operatively connected to the sensors 62.

According to the embodiment shown in FIG. 7 the device also comprises an ultrasonic transducer 77 by means of which the effect of the dispersion or e.g. whey upon ultra waves transmitted by means of said transducer is detected. The ultrasonic transducer 77 operates as a supplement to the acoustic spectroscopy means 61, 62. Also the transducer 77 should be operatively connected to the multivariate analysis unit 69 such as shown in FIG. 7. Alternatively it may be directly operatively connected to the process control and adjustment unit 610.

The acoustic waves will cause a perturbation in the liquid dispersion, and there will be subsequent pulses of dispersion subjected to a high and low pressure respectively. As seen in FIG. 4 the acoustic transmitter will generate a dynamic pressure wave of alternating positive and negative pressures around a (large) mean value in the dispersion. The acoustic wave will have a much lower frequency (0–20 kHz) than the ultrasonic wave (more than 100 kHz). This allows many ultrasound measurements, transmitting and receiving an ultrasound signal, being made during one time period of the acoustic signal.

For the example of a sine wave, the acoustic pressure will be positive during half of the period and negative during half of the period (FIG. 4). This allows ultrasound measurements to be made both for positive and negative acoustic pressure (FIG. 5). If the measured ultrasound response of the fluid during positive is different from the measured ultrasound response of the fluid when the acoustic pressure is negative, the difference between those two signals will give additional information about the fluid properties. The resulting data is by nature two dimensional, which allows three-way multivariate data analysis, which increases the robustness of the method.

It should be understood that a plurality of alternative embodiments will be obvious for a man skilled in the art, all of which however will be within the scope of the invention as defined in the appended claims supported by the description and the accompanying drawings.

The principle of using acoustic spectroscopy for denaturation, homogenisation or crystallisation processes in which the acoustic sound transmitter 61 and the sensors 62, as well as the ultrasonic transducer 77, have a different position or are arranged differently with regard to the described embodiment are all covered by the invention.

For example, the tube 68 does not need to be a process line tube, but could as well be any measurement tube or loop arranged just for measurement purposes. It might not even be a tube, even though that is the preferred design. The invention is applicable also to batch processes in which the inventive method may be applied to dispersions processed in a vessel or the like.

It should be mentioned that the ultrasonic transducer should have a well defined geometry, preferably a rectangular cross section with plane surfaces perpendicular to the ultrasonic waves transmitted into the dispersion.

The application of the inventive method and device for controlling and monitoring denaturation of proteins in whey, homogenisation of fat droplets, or crystallisation of crystals, in a dispersion has been described by way of example. Examples of process applications and/or products produced therefrom in which the inventive method and device are applicable are; for monitoring and controlling the consistence of acidified dairy products in acidifying processes; for monitoring and controlling the homogenisation process and cooling process to obtain a controlled low-fat margarine product, by monitoring fat content and to some degree fat droplet size in the dairy product thereby produced; for monitoring and controlling the free fat content in dairy products such as cream and UHT products (ultra high temperature treated products for long lifetime) during the production thereof, and: for monitoring and controlling the particle size distribution of fatty droplets in, for example, ice cream or any other milk-based product. Different process parameters such as temperature, pH, pressure, etc. may then be controlled based on the results of the monitoring by means of acoustic spectroscopy in a suitable way.

The application of the inventive method and device for monitoring and controlling fermentation process has been described by way of example. It is evident that a man skilled in the art would be able to derive from the above information a plurality of alternative embodiments all of which are still within the scope of invention as defined in the enclosed patent claims supported by the description and the accompanying drawing.

For example, it should be realised that the invention is applicable to arrangements for continuous fermentation as well as the batch wise process described above by way of example.

What is claimed is:

1. A method for monitoring and controlling viscosity and/or aggregate size and/or content of dispersions of proteins, crystalline particles or fat droplets during processing, the method comprising:

monitoring at least a part of the proteins and/or crystalline particles and/or fat droplets with acoustic spectroscopy utilizing acoustic waves having a frequency range of 0 to 20 kHz.

2. The method according to claim 1, wherein the process is controlled by means of heat and/or pH and/or pressure adjustment based on the result of the acoustic spectroscopy.

3. The method according to claim 1, wherein the dispersion subjected to the acoustic spectroscopy is conducted through a tube.

4. The method according to claim 1, wherein the acoustic waves that the dispersion is subjected to are transmitted in a direction along the axis of the tube.

5. The method according to claim 1, wherein the dispersion comprises proteins subjected to denaturation in a process for preparing a food product.

6. The method according to claim 1, wherein the dispersion comprises proteins subjected to denaturation in a process for preparing a dairy product.

7. The method according to claim 1, wherein the dispersion comprises fat droplets subjected to a homogenisation process of preparing a food product.

8. The method according to claim 1, wherein the measurement by means of acoustic spectroscopy is an on-line measurement executed in a process line in which said process takes place.

9. The method according to claim 1, wherein the dispersion is also subjected to an ultrasonic measurement and that the process is controlled based on the acoustic spectroscopy with regard taken to the result of the ultrasonic measurement.

10. A device for monitoring and controlling viscosity and/or aggregate size and/or content of a dispersion of proteins, crystalline particles or fat droplets during processing thereof, the device comprising:

a means for subjecting the dispersion to acoustic spectroscopy utilizing acoustic waves having a frequency range of 0 to 20 kHz.

11. The device according to claim 10, wherein it comprises a tube through which the dispersion flows while being subjected to the acoustic spectroscopy.

12. The device according to claim 10, wherein the tube is a tube in a process line for the production of a food product.

13. The device according to claim 10, wherein it comprises an ultrasonic transducer for transmitting ultrasonic waves through the dispersion that is subjected to the acoustic spectroscopy.

14. Use of acoustic spectroscopy for monitoring a process, the use comprising detecting a state of the process by monitoring viscosity and/or aggregate size and/or content of dispersions of proteins, crystalline particles or fat droplets that are processed, wherein the acoustic spectroscopy utilizes acoustic waves having a frequency range of 0 to 20 kHz.

15. Use of acoustic spectroscopy for monitoring a process, which is a process for the production of a food product, the use comprising monitoring the product with acoustic spectroscopy utilizing acoustic waves having a frequency range of 0 to 20 kHz.

16. The method according to claim 1, wherein the acoustic waves have a frequency range of 100 to 5000 Hz.

17. The method according to claim 1, wherein the acoustic waves have a frequency range of 100 to 3300 Hz.

18. The device according to claim 10, wherein the acoustic waves have a frequency range of 100 to 5000 Hz.

19. The device according claim 10, wherein the acoustic waves have a frequency range of 100 to 3300 Hz.

20. The method according to claim 6, wherein the process is a process in which whey is denatured.

21. The method according to claim 7, wherein the product is a dairy product.

22. The device according to claim 12, wherein the product is a dairy product, and wherein the process is a process in which whey is denatured or a dairy product is homogenised.

23. The use according to claim 15, wherein the product is a dairy product, and the process is a process in which whey is denatured or in which fat droplets are homogenised.

* * * * *